United States Patent [19]

Hagio et al.

[11] Patent Number: 4,909,796
[45] Date of Patent: Mar. 20, 1990

[54] MEDICAL GUIDING MICROTUBES

[76] Inventors: Mitsuyuki Hagio, 1-31-22, Tsu-nishi, Kamakura-shi, Kanagawa-ken; Yasuhiko Futami, 12-7-1010, Nakameguro 4-chome, Meguro-ku, Tokyo; Noriyasu Noguchi, 2229-83, Koshinohara, Yasu-cho, Yasu-gun, Shiga-ken; Ryusaku Yamada, 1-10, Masago-cho, Wakayama-shi, Wakayama-ken, all of Japan

[21] Appl. No.: 349,912

[22] Filed: May 9, 1989

Related U.S. Application Data

[63] Continuation of Ser. No. 923,846, Oct. 28, 1986, abandoned.

[30] Foreign Application Priority Data

Jan. 11, 1985 [JP] Japan .................. 60-2131

[51] Int. Cl.⁴ ............................................. A61M 25/00
[52] U.S. Cl. ...................................... 604/247; 604/96; 137/852; 606/194
[58] Field of Search .............. 604/247, 96–103, 604/52–53, 170; 128/656–658, 325, 348.1, 344; 137/852

[56] References Cited

U.S. PATENT DOCUMENTS

| 2,746,477 | 5/1956 | Krause et al. | 137/852 |
| 4,029,104 | 6/1977 | Kerber | 128/656 |
| 4,085,757 | 4/1978 | Pevsner | 128/325 |
| 4,213,461 | 7/1980 | Pevsner | 128/656 |
| 4,301,803 | 11/1981 | Handa et al. | 128/658 |
| 4,341,218 | 7/1982 | Ü | 128/325 |
| 4,402,319 | 9/1983 | Handa et al. | 128/325 |
| 4,413,989 | 11/1983 | Schjeldahl et al. | 604/104 |
| 4,471,779 | 9/1984 | Antoshkiw et al. | 128/325 |
| 4,616,653 | 10/1986 | Samson et al. | 128/348.1 |
| 4,619,274 | 10/1986 | Morrison | 604/170 |
| 4,646,742 | 3/1987 | Packard et al. | 128/348.1 |

*Primary Examiner*—Dalton L. Truluck
*Assistant Examiner*—Denise W. DeFranco
*Attorney, Agent, or Firm*—Scully, Scott, Murphy & Presser

[57] ABSTRACT

A medical guiding microtube in which at the tip of a synthetic resin tube a balloon having substantially the same outer diameter as said tube is attached and a ball-like body connecting at the tip of said tube through yarn in defined length is provided within the balloon having optionally a hole for leaking fluid, and it can be safely introduced to peripheral blood vessel and when used as leak balloon catheter it can control precisely and in good reproducibility a timing for leaking therapeutic liquid.

4 Claims, 3 Drawing Sheets

MEDICAL GUIDING MICROTUBES

This application is a continuation of application Ser. No. 923,846, filed 10-28-86, which is a continuation of International application PCT/JP86/00007, filed Jan. 10, 1986, which designated the U.S. of America.

BACKGROUND OF THE INVENTION

An angiography in which lesions on blood vessels are diagonosed by injecting a contrast medium into the blood vessel and studying the flow and expansion of the contrast medium and a topical administration therapy in which therapeutic liquid is injected into the blood vessel have been widely carried out by the development of Seldinger's method in which catheter is inserted into blood vessel transdermally.

Heretofore, the catheter used for injecting therapeutic liquid into lesions on blood vessels has been used by firstly introducing a guide wire thereof within the blood vessel near the lesion and then inserting the catheter along the outer wall of the guide wire. As the guide wire, in general, a metal guide wire of stainless steel and stainless steel coil has been used and has drawbacks such as liability to injuring the inner wall of blood vessel during operation. Recently so called flow guide wire, of which tip is floated on the blood flow and introduced into peripheral blood vessels, has been proposed, but it also has drawbacks, for example, in which the structure is so fine that it is difficult to pass through such blood vessels having many windings and bendings and it is substantially impossible to introduce it up to a lesion of peripheral blood vessels. Also, a guide catheter which can perform the roles of both catheter and guide wire and well known leak balloon catheter have drawbacks, for example, the liability to injuring the inner wall of blood vessels, the difficulty of passing through peripheral blood vessels and the instability of the operation.

SUMMARY OF THE INVENTION

The object of the present invention is to present a flow guide wire and/or a flow guide catheter (called as a guiding microtube hereinafter) which improve the disadvantages of the above prior art.

Another object of the present invention is to present a flow guide wire which can be selectively introduced into peripheral blood vessels by simple handling in short time and be easily withdrawn and further be handled very safely.

Another object of the present invention is to present a flow guide catheter particularly a leak balloon catheter which can easily be introduced into peripheral blood vessels and be handled safely by controlling the infusion of therapeutic liquid easily and certainty.

The fundamental structure of the guiding microtube of the present invention is a cylindrical or spheroidal balloon which is projectingly attached to the tip of a plastic tube.

More specifically, the guiding microtube of the present invention comprises a plastic tube having a fluid outlet hole at the tip of the tube and a fluid inlet hole near the rear end of the plastic tube, said plastic tube having optionally a fine tip portion, thick operational portion and taper portion connecting both, making an inside portion of said tube a fluid transfer channel, said channel optionally containing non-X ray transmission material so that the function of said fluid transfer channel is maintained, attaching a cylindrical or spheroidal balloon at the tip of said tube so as to interconnect the lumen of said balloon with said fluid outlet hole, optionally providing a fluid outlet hole at the tip of said balloon and providing a valve mechanism within the lumen of said balloon when the fluid outlet hole is provided at the tip of said balloon.

The guiding microtube of the present invention may perform function of a flow guide wire and/or a leak balloon catheter. When used as the flow guide wire, said tube has a slender tip portion, a thick operational portion and taper portion interconnecting them, and contains non-X ray transmission material within it. When used as a leak balloon catheter, a fluid outlet hole is provided to the balloon having a value mechanism. Said valve mechanism comprises a movable stopper which is engaged with the catheter, and said stopper makes said outlet hole of therapeutic liquid open or close according to the transformation of said balloon caused by the change of the inner pressure of said balloon to form a valve mechanism.

To understand the invention, the illustration will be given to a guiding microtube used as a flow guide wire.

BRIEF DESCRIPTION OF THE DRAWINGS

FIGS. 1–3 show the guiding microtube of the present invention suitable for the use as flow guide wire:

FIG. 2 is an elevation cross sectional view of a structure wherein non-X ray transmission material 3' is contained in the tip of the lumen of a balloon;

FIG. 3 is an elevation cross sectional view of a structure wherein flexible and slender material is used for a synthetic resin tube 1 and the flexible portion and taper portion are shortened;

FIGS. 4–7 show a guiding microtube of the present invention suitable for the use as leak balloon catheter:

FIGS. 5, 6 and 7 are elevation views of the tip portions of other embodiments.

FIG. 1(a) shows an elevational cross sectional view of the fundamental structure of the flow guide wire of the present invention, and FIGS. 1(b) and (c) show cross sectional views of FIG. 1(a) at part A–A' and part B–B', respectively.

Figure 1A:
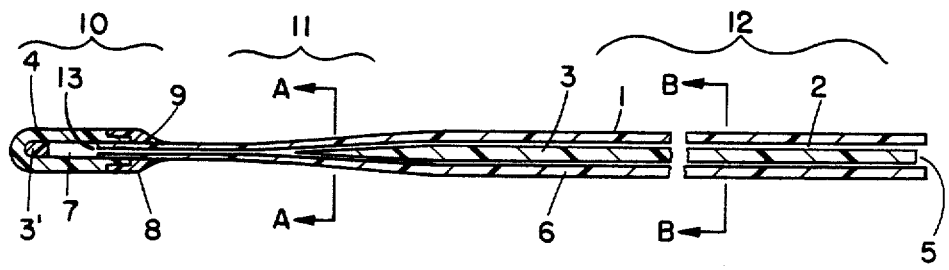
FIG. 1(a) is an elevation cross sectional view of the fundamental structure thereof.
Figure 1B:
FIG. 1(b) is a cross sectional view of part A–A' in FIG. 1(a)
Figure 1C:
FIG. 1(c) is a cross sectional view of part B–B' in FIG. 1(a)

The flow guide wire of the present invention comprises a plastic tube 1 having an empty portion 2 which is opened throughly, non-X ray transmission material 3 and a balloon 4. In the tube 1, from this tip to the rear end, there are a slender and flexible tip portion 10, a taper portion 11 and a relatively thick and hard operational portion 12 succesively. The non-X ray transmission material 3 is inserted into the empty portion 2 from the rear end of the operational portion 12 to the taper portion 11, being fixed at the rear end of the operational portion 12 by any method. A fluid outlet hole 13 is provided at the tip of the tube 1 and a fluid inlet hole 5 at the rear end thereof; and at the end of flexible tip portion 10 an elastic balloon 4 containing non-X ray transmission material 3' is attached independently and projectingly, and the lumen 7 of said balloon is interconnected with the fluid inlet hole 5, the fluid outlet hole 13 and the fluid transfer channel 6.

Usually the fluid inlet hole 5 is capped and preferably may be connected with a connector or an injector.

Figure 2:
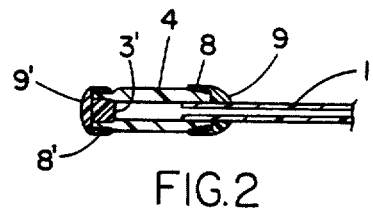

FIG. 2 is an elevation cross sectional view of another embodiment of the balloon, and in this case, a balloon 4 is cylindrical, its tip being closed with non-X ray transmission material 3' fixed with fiber 8' and adhesive 9' etc.

Figure 3:
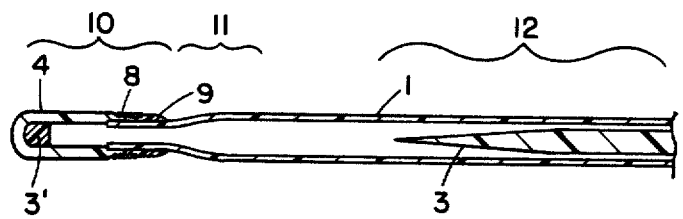

FIG. 3 shows a tube 1 in which a flexible and slender material is used and a flexible portion and taper portion are shortened.

The structures of each part of the flow guide wire of the present invention will be illustrated hereinafter.

The balloon 4 is made of elastic cylindrical or spheroidal rubber latex, silicone rubber, urethane elastomer etc. in uniform thin membrane. In the flow guide wire of the present invention, the membrane of the balloon may be as much as about 250 μm thickness and its pressure resistant property can be improved compared with the one used in above flow guide wire, because the size of the balloon can be smaller before dilatation.

A small hole through which normally fluid can not be passed may be provided at a part of the balloon 4 to prevent bursting of the balloon 4.

The balloon 4 is attached so as to cover the flexible tip portion 10 of the tube 1, and the covered part is fixed by fastening tightly with fiber 8 of silk, nylon, polyester or urethane elastomer on the rubber and finished to have smooth and even surface by applying adhesive 9 to the surface. It is preferred to contain non-X ray transmission material at the tip of the balloon 4 as shown in the Figure, but it is not always necessary.

The fluids to dilate the balloon 4 include liquids such as physiological saline or blood vessel contrast media or gases such as carbon dioxide, and they are introduced under pressure into the lumen 7 of the balloon via the fluid transfer channel 6 and the fluid outlet hole 13 from an injector or a connector which is connected with the fluid inlet hole 5 in order to dilate the balloon 4.

The tube 1 having the empty portion 2 has even and smooth surface overall, its tip being finished slenderly to be flexible. From the rear end of the operational portion 12 to the taper portion 11 in the empty portion 2, there is contained non-X ray transmission material 3 which is processed taperingly so as not to choke the empty portion of the taper portion which is increasingly more slender. The fluid inlet hole 5 is provided at the rear end.

As the material of the tube 1 any melt spinnable or extrusion moldable plastic materials may be used, and polyamide, polyester, polyolefin or Teflon are preferably employed.

The diameter of the empty portion 2 of the tube 1 is desirably larger, and it is necessary for even the structure from the taper portion 11 up to the flexible tip portion 10 which cannot be made larger in order to maintain tensile strength to be more than 0.15 mm.

The sizes of each portion of the tube 1 may depend on the age or body of the patient and severity of the illness and cannot be defined specifically. The normal typical sizes will be given below.

TABLE 1

|  | Outer diameter (mm) | Length (mm) |
| --- | --- | --- |
| Tube | 0.3~1.0 | 400~2600 |
| Flexible tip portion | 0.3~0.6 | 20~50 |
| Taper portion | — | 30~80 |
| Balloon | 0.3~1.0 | 2~6 |

The non-X ray transmission material 3 used in the present invention are metal wires having superior angiographic formation by X ray radiation such as gold, stainless steel or tungsten. The metal wires are processed taperingly so as not to choke the empty portion of the taper portion 11 but in other portions they have diameters of 20–80% of the inner diameter of the empty portion in the operational portion.

A method of producing a flow guide wire of the present invention will now be given.

For a tube prepared by melt spinning method or extrusion molding method, a portion corresponding to flexible tip portion is formed by drawing it with heating, then the taper portion is formed by drawing suitably, and cut in desired length.

The cut end of the flexible tip portion is slightly opened by heating. To this end, a balloon made of rubber latex which had been separately prepared by coagulation method contained non-X ray transmission material 3' at the tip is covered, and if necessary, after ensuring fixation by applying adhesive, it is fastened tightly with fiber 8 as described above, and on the fiber the adhesive 9 is applied on the surface to finish it smoothly and the surface is finished to have gentle grade to complete the attachment of the balloon 4. Finally, from the rear end of the operational portion, non-X ray transmission material 3 processed taperingly is inserted and fixed at the rear end of the tube 1. As the fixation method, non-X ray transmission material 3, wound beforehand, is engaged with the empty portion 2, or adhesive is introduced into the empty portion 2 to fix the non-X ray transmission material 3 on the inside wall of the tube 1. The fluid inlet hole 5 is provided on the side of the tube by boring a hole in the side wall of the tube with a micro drill and if necessary, a connecting terminal such as a cap or a connector is provided to obtain the flow guide wire of the present invention.

When a silicone or Teflon coating is applied on the outer surface of the flow guide wire, good movement between the catheter and the wire may be obtained and anti-thrombus formation property can be improved.

The expanded balloon of the flow guide wire of the present invention is introduced to peripheral blood vessel by way of blood flow to lead the guide wire. While an operator observes the image of the balloon by X ray radiation by a monitor, he can have its tip arrive at the target lesion of the blood vessel more selectively.

In the flow guide wire of the present invention, the thickness of the membrane of the balloon can be greater, and durability against expansion and shrinkage is improved. Thus, before the flow guide wire is inserted into the blood vessel, the air in the lumen of the balloon can be replaced with the liquid of the contrast medium for expansion of the balloon, and the confirmation of the balloon at the tip is very easy in use. By controlling the size of the balloon by means of the adjustment of the amount of the fluid pressured from the fluid inlet hole 5, the tip of the flow guide wire is not inserted into other blood vessels than the target one through mistake, and can easily reach the lesion on the blood vessel within a short period. In this case, the guide wire of the present invention does not injure the wall of blood vessel because it is soft.

The non-X ray transmission material 3 contained in the empty portion 2 of the tube 1 gives suitable hardness to the flow guide wire to obtain good operability, and the image represented through a monitor by X ray radiation is so fine that the position of the non-X ray transmission material 3' at the tip can be easily found.

Since in the flow guide wire of the present invention the balloon 4 at the tip is greatly dilated and movable freely according to blood flow, it is easily passed through winding blood vessels and can reach the lesion on a peripheral blood vessel selectively. The balloon 4 is further dilated at the reached site, so that the tip of the flow guide wire is fixed at the wall of the blood vessel. Therefore, the transfer of the tip of the guide wire by the movement of the blood vessel and the insertion of the catheter is prevented, and the blood vessel is formed straight by pulling the guide wire to make the insertion of catheter easy. According to the present invention, better results are obtained for the diagnosis and treatment by catheterization.

Using the flow guide wire of the present invention, the operation can be more conveniently carried out than the use of prior flow guide wires when it is withdrawn from the catheter, because the tip portion is smaller than the operational portion.

The structure of the leak balloon catheter of the present invention will be explained hereinafter. In the following illustration, the use of fiber is described as the means of engaging a removable stopper with a catheter, but the present invention is not always limited to the use of fiber. As other engaging means than the fiber, there are the use of a spring etc. or the use of a stopper of which fine tail is molded together to engage with the body of the catheter. In this specification, "engage with the body of the catheter" does not always mean that it engages directly with the body of the catheter, but the stopper is not apart from the tip of the body of the catheter more than a definite distance.

Figure 4A:
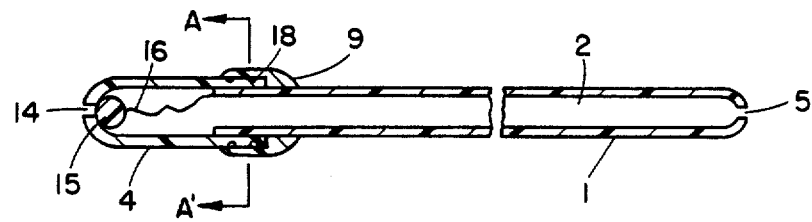
FIG. 4(a) is an elevation view of the fundamental structure thereof.
Figure 4B:
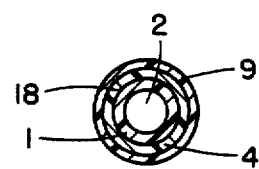
FIG. 4(b) is a cross sectional view of part A–A' in FIG. 1(a)

FIG. 4 is an elevation view (a) and a cross section view (b) of an embodiment of the leak balloon catheter of the present invention. This comprises a balloon 4 which is a flexible elastic material and provided with a fine fluid outlet hole 14 at the tip, said balloon attaching to the tip of the tube 1 which has an empty portion 2 and is the body of the catheter.

Within the lumen of the balloon 4 there is a stopper 15 which contacts directly with a fluid outlet hole 14 for exiting therapeutic liquid, and one end of fine fiber 16 is fixed at the stopper 15 while another a little loosened end of it is fixed in adhesive 9 through the engagement between the tube 1 and the balloon 4. All of these composes a valve mechanism which will be described below.

The engagement portion of the balloon 4 and the tube 1 is fastened with fiber, and in order to avoid abnormal storage of blood, the knots and unevenness are finished smoothly with adhesive 9 and the difference between the rear end of the balloon and the catheter is finished to gentle grade.

Figure 5:
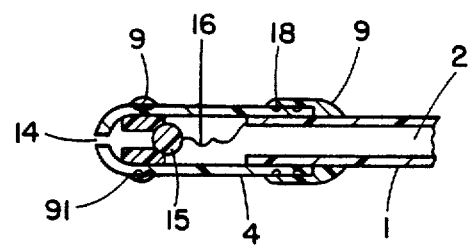

A small fluid inlet hole 5 for introducing therapeutic liquid is provided at the operational portion of the tube 1, and is interconnected with the empty portion 2 and the lumen of the balloon, and the empty portion 2 is utilized as a fluid transfer channel. FIG. 5 shows an elevation view of an embodiment in which a pipe 91 comprising non-X ray transmission material (usually metal) is inserted between a fluid outlet hole 14 and a stopper 15.

Figure 6:
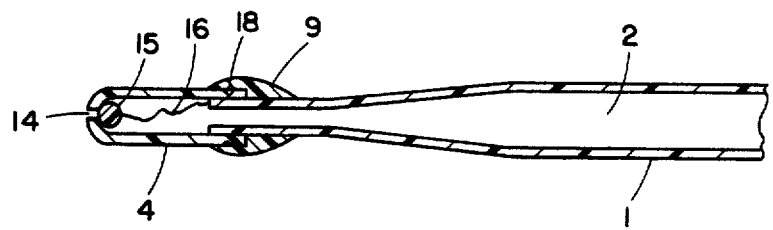
Figure 7:
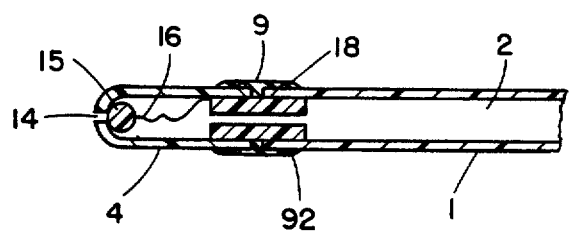

The pipe 91 inserted is fixed by fastening with fiber 18 on the outer circumference of the balloon 4. FIG. 6 shows an embodiment in which the balloon 4 is attached to the tip of the tube by narrowing the outer diameter of the latter through drawing, the outer diameter of the attached balloon 4 being the same as that of the tube 1. FIG. 7 is an elevation view of an embodiment in which a pipe 92 comprising non-X ray transmission material is employed for the connection between the tube 1 and the balloon 4. In FIG. 7, the tube 1 and the balloon 4 are capped from both ends of the pipe 92 comprising non-X ray transmission material along with their outer walls, and the outer circumferences of the tube 1 and the balloon 4 are fastened with yarn 18 to fix on the pipe 92. The knots of yarn and the unevenness of the connection are made smooth with adhesive 9. In this case, the yarn 16 connected with a valve mechanism is fixed between the pipe 92 and the balloon 4, and a stopper 15 engages with the tube 1.

The structures of each part of a leak balloon catheter of the present invention will now be illustrated.

The balloon 4 attached at the tip of the tube 1 is an empty elastic body having a circular cross section which is oblongly cylindrical or spheroidal as well as flexible, and it has a sufficient strength not to be cut when dilated and introduced to the lesion by means of blood flow.

At the tip of the elastic balloon 4, a fine fluid outlet hole 14 is bored. A stopper 15 which contacts directly from the lumen of the balloon 4 with the pipe 91 comprising non-X ray transmission material and positioned at or in front of the fluid outlet hole 14 is a ball of which diameter is by about 50% larger than that of the outlet hole of fluid 15 and is smaller than that of the lumen of the balloon 4. The yarn 16 connecting them is fine and flexible so that the movement of the stopper 15 is free, and is loosened while the balloon 4 is not yet dilated, and its end is fixed between the tube 1 and the balloon 4, and has strength enough not to be cut under the pressure of the therapeutic liquid stream. The diameter of the yarn 16 is preferably about 10–40 $\mu$m. The fluid inlet hole 5 near the operational portion of the tube 1 is normally covered with a cap, and has a structure equipped with a connector or an injector.

The material of the tube comprising a catheter is not particularly limited, but melt extrusion moldable tubes such as one of synthetic resins such as polyamides, polyesters, polyolefins and fluororesins are preferably used. As the catheter used for diagnosis and treatment of blood vessels within the brain is required to be soft, silicone and polyurethane are suitably used.

For the elastic balloon 4 attached at the tip, very flexible rubber latex, silicone rubber or urethane elastomer are preferably used. The balloon of rubber latex coated with silicone oil is preferred, because it prevents degradation or formation of thrombus in contacting with blood. The thinner elastic body, for example, having the thickness of less than 300 $\mu$m preferably less than 200 $\mu$m is suitable. The diameter of the fine fluid outlet hole 14 is about 100–400 $\mu$m, since it becomes larger by dilatation even if it is usually smaller.

The therapeutic liquids used for dilatation of the balloon include physiological saline or contrast media, and they are extruded through the fluid outlet hole 14.

The size of each part of the leak balloon catheter of the present invention may be dependent on age of patient, physical constitution, severity of illness etc. and cannot be particularly defined. The normal typical sizes will be given as follows.

TABLE 2

|  | Diameter (mm) | Length (mm) |
|---|---|---|
| Tube | 0.5~3.5 | 600~2500 |
| Balloon | 0.4~5.0 | 4~10 |
| X ray Non transmission metal pipe | 0.5~2.5 | 1~4 |

The ball-like body used for a stopper 15 comprising a valve mechanism of the leak balloon catheter of the present invention may be of silicone or other synthetic resins, and stainless steel or steel, the latter two being preferred because of easy processing for boring a hole connected with yarn. When it is placed directly contacting with the pipe 91 consisting of non-X ray transmission material in FIG. 5, silicone coating on the surface of the ball-like body is suitable because of close contacting.

In FIG. 5, as the pipe 91 consisting of non-X ray transmission material has a hole, the fluid outlet hole 14 is not always necessary for the balloon. When the tip of the balloon is opened, the operation should be careful because the therapeutic liquid remained in the lumen of the pipe is dried and clogged by withdrawing the air in the lumen of the catheter before use.

The non-X ray transmission materials used herein include pipes of metals having superior angiographic formation by X ray radiation, typically gold or platinum, and metals being stable in therapeutic liquid are preferred. Alternatively there are pipes used with rigid synthetic resin as materials which are coated with a mixture of metal powder having angiographic formation ability by X ray radiation such as tungsten or tantalum etc. and adhesive, but in the absolute concentration of metal the above pipes are better.

0.2-0.6 mm of the diameter of hole of the pipe can be used without any difficulty of passing through therapeutic liquid. When the plane of the pipe 91 contacting with the stopper 5 is made to be conical, it is more convenient because of greater contacting area with the ball-like body.

The stopper 15 used for a valve mechanism normally contacts with the fluid outlet hole 14 or the pipe 91 comprising non-X ray transmission material from the lumen of the balloon 4, and when therapeutic liquid is injected into the lumen of the balloon 4 from the empty portion 2 which is a fluid transfer channel of the tube 1, it is at first pressed toward the fluid outlet hole 14 by the pressure of the liquid.

As the therapeutic liquid is injected, the balloon begins to dilate because of no outlet, and finally it becomes dilated towards the direction in which the length of the balloon elongates. The yarn of the stopper under pressure elongates pressed with the fluid outlet hole 14 while the yarn 16 maintains its looseness, but when the yarn 16 is stretched by the elongation of the balloon 4, the stopper 15 is apart from the fluid outlet hole 4, and the fine hole opens and the leak of the therapeutic liquid begins. Then even when the injection of therapeutic liquid stops, the leak of therapeutic liquid continues for some time under the pressure from shrinkage of the balloon 4. In time the lengthwise shrinkage of the balloon 4 begins. In this case, since the stopper 15 receives the pressure of therapeutic liquid which continues to leak, the yarn 16 is maintained stretched, and then the stopper 15 contacts with the fluid outlet hole 14 to choke up and stop the leak of therapeutic liquid. The form of the balloon is maintained as long as the injection pressure does not change.

EXAMPLES

The examples will be given below to illustrate the present invention further.

Example 1 (Flow guide wire)

Using polyester as material, a hollow tube having an 0.8 mm outer diameter and a 0.4 mm inner diameter hollow portion was prepared by conventional melt spinning through hollow spinneret, and was cut into a length of 1.5 m. Then the tip portion of said tube was drawn by heating with steam to obtain a soft and fine tip portion having 0.4 mm outer diameter and 0.25 mm inner diameter hollow portion in a length of about 3 cm. The tip was formed slightly conically by heating, and was covered with a rubber latex tube which had be separately prepared by coagulation method and cut into the desired length, and then they were fastened tightly with polyurethane elastic yarn. From the tip of the rubber latex tube, a gold wire having a 0.4 mm diameter and 1.5 mm length was inserted, and it was fixed by fastening tightly with polyurethane elastic yarn on the outer surface of the rubber latex tube. From the rear end of the polyester tube 1.45 m of a tungsten wire of which the tip has been processed to taper form was inserted up to the taper portion, and the rear end of the tungsten wire was wound and inserted into the rear end of the empty portion of the polyester tube to fix on the inner wall of the empty portion. The tip portion of the balloon fastened with polyurethane yarn and the exposed portion of the gold wire was made smooth and round with epoxy resin and unevenness was also made gentle grade, and the balloon and polyester tube were applied with silicone coating, and further a detachable connector for connecting with syringe was attached on the fluid inlet hole at the rear end to give the flow guide wire of the present invention.

After sterilization of the flow guide wire with ethylene oxide gas, the wire was inserted into a blood vessel from the femoral artery by Seldinger's method, and reached lower mesenteric artery from abdominal aorta. The balloon was dilated to 4 mm diameter and made free by floating on blood flow. It floated on the blood flow to reach gastro-duodenal artery. Alternately, the flow guide wire of the present invention was dilated into 4 mm diameter at the entrance of abdominal artery, and entered into inherent hepatic artery by floating in blood flow to reach the lesion of peripheral blood vessel of right hepatic artery. The balloon was further dilated and fixed on the inner wall of the blood vessel to introduce the catheter without slipping off the tip of the guide wire. Consequently, it was possible that the catheter was inserted to the lesion and good therapeutical effect was obtained.

Example 2 (Leak balloon catheter)

As shown in FIG. 4(a), a stopper 15 in which nylon yarn 16 having diameter of 0.03 mm had been fixed with adhesive on a stainless steel ball of 0.3 mm diameter with adhesive (Sankyo Pharmaceutical Co.: "ARON αA") was inserted into the lumen of a balloon 4 in which a fine hole had been bored with sharp-pointed piano wire of 0.2 mm diameter at the tip of the rubber latex having a 0.4 mm inner diameter, 0.15 mm thickness and 4 mm length. At the tip of a catheter comprising polyethylene tube of 0.1 mm inner diameter, 0.6 mm outer diameter and 700 mm length, the balloon 4 having nylon yarn 16 of about 4 mm in length was attracted. Two parts of the engaged balloon was fixed by fastening tightly, and then two-liquid type epoxy resin (Cemedine Co., "High-Super") was applied and the surface was finished smoothly. Into the opening portion of the operational portion of the tube a 25 G injection syringe was inserted to give a leak balloon catheter.

Physiological saline was injected into the leak balloon catheter through a fluid inlet hole equipped with 25 G injection syringe attached with a three way choke from an injection cylinder of volume of 2.5 ml, and the balloon was dilated at about 2.0 kg/cm². When the valve was closed, the balloon maintained the form, and no leak from the fluid outlet hole was noticed.

Example 3 (Leak Balloon catheter)

In FIG. 5, a stopper 15 in which nylon yarn 16 of 0.04 mm diameter had been fixed with adhesive on a stainless steel ball 0.3 mm diameter and the surface had been coated with silicone (Toray Silicone: "SH781") was inserted into the lumen of a rubber latex balloon 4 having 0.4 mm inner diameter, 0.2 mm thickness and 5 mm length. At the tip of the balloon 4 a fine hole was stored with sharp-pointed piano wire of 0.2 mm diameter, and within the lumen inserted was a gold pipe 91 having a 0.2 mm inner diameter and a 0.5 mm outer diameter of which one end of the lumen had been finished conically with very fine drill, the insertion being done from another unfinished end. The balloon 4 containing such valve mechanism and having nylon yarn of about 4 mm in length attached at the tip of a tube 1 in which 6 cm of the tip of a polyester tube having a 0.4 mm inner diameter, 0.18 mm outer diameter and 1,500 mm length had been elongated by heating and processed taperingly so as to be larger towards the operational portion. The engaging portion and the gold pipe inserting portion were fixed on the circumference of the balloon by fastening with polyurethane yarn, and further with two-liquid type epoxy resin (Nagase-Ciba: "ARALDITE" "HARDNER") to finish smoothly, and unevenness between the balloon and the catheter was made gentle grade. From the opened operational portion of the catheter, a tapered tungsten wire having 0.3 mm diameter was inserted, and at the opening 25 G injection syringe was inserted, the space being filled with epoxy resin. All of the catheter was coated with silicone (Dow-Corning: "MDX4-4159") to give the leak balloon catheter.

After sterilization with ethylene oxide gas, it was used for clinical test in which it was inserted from femoral artery to hepatic artery via abdominal artery.

For the leak balloon catheter of the present invention inserted into femoral artery by Seldinger's method, the balloon was not dilated from femoral artery to abdominal artery, but contrast medium ("Andiographin") was injected under pressure through an injection syringe at the fluid inlet hole 2 from an injection cylinder filled with the medium through abdominal artery to hepatic arteries to dilate the balloon which floated in blood flow. Adding slight pressure to dilate the blood vessel itself, it easily reached left hepatic artery and the injection of therapeutic liquid (antitumor agent) could be done. The gold pipe 91 at the tip portion could be visually traced by an X ray radiation monitor, and when the leak balloon catheter was withdrawn, it could be cleaned only by wiping with gauze and no blood was noted.

The leak balloon catheter of the present invention can float on blood flow and move freely by adjusting the size of the balloon depending on the state of the blood vessel of the patient after the insertion into the blood vessel. By this function, the guiding ability of the balloon is remarkably improved, and the balloon can reach the peripheral part without or injuring the inner wall of a blood vessel even at the branched part of blood vessel. Therefore, the burden on the patient is not only relieved, but the concern of the operator is remarkably lightened. When a contrast medium is used for the dilatation of the balloon, observation by monitor is definite, and therapeutic liquid is readily replaced and injected when it reaches the lesion and the therapeutic liquid is injected under pressure. Using a pipe of non-X ray transmission metal at the tip, even at the injection of therapeutic liquid, the case in which the tip of the catheter is transferred to another blood vessel can be easily found by the movement of the blood vessel and the operation can be amended.

Since the infusion of therapeutic liquid can be carried out maintaining the dilated tip balloon, it is possible to effect the infusion under limitation or choking up of blood flow.

This results in decrease of the infusion amount and the effect of side complication, and in a method of forming angiographic image in blood vessel little vagueness in angiographic image is obtained to decrease misdiagnosis.

As the surface of the catheter is smooth and unevenness is finished smoothly, there is no stagnation of blood flow and by coating with silicone the formation of thrombus is also prevented.

What is claimed is:

1. A medical guiding microtube which comprises a plastic tube having a first fluid outlet hole at a forward tip of the tube and a fluid inlet hole near an opposite end of the plastic tube, said plastic tube having a fine tip portion, a thick operational portion and a taper portion connecting both, an inside portion of said tube comprises a fluid transfer channel, said channel containing non-X-ray transmission material in said portion, a cylindrical or spheroidal balloon attached at the tip portion of said tube so as to interconnect the lumen of said balloon with said fluid outlet hole, said balloon being provided with a second fluid outlet hole at the tip of said balloon opposite said first fluid outlet hole of said tube, said balloon being further provided with a movable ball-shaped stopper within the lumen of said balloon, said stopper being engaged with the forward tip of said tube by means of yarn to control opening and closing of said second fluid outlet hole upon an increase and decrease, respectively, in the inner pressure of said balloon.

2. A medical guiding microtube suitable for use as leak balloon catheter which comprises a plastic tube having a first fluid outlet hole at a forward tip of said tube and a fluid inlet hole near a rear end of said tube, respectively, a cylindrical or spheroidal balloon being provided at the forward tip of said tube so as to interconnect the lumen of the balloon with said fluid outlet hole, said balloon being provided with second fluid outlet hole at the tip of said balloon and a removable stopper in the lumen of said balloon, said stopper comprising a ball-shaped member engaged with the forward tip of said tube by means of yarn for opening said second fluid outlet hole upon an increase in the inner pressure of said balloon and for closing said second fluid outlet hole upon a decrease in the inner pressure of said balloon.

3. A medical guiding microtube according to claim 2, wherein a pipe comprising non-X ray transmission material is provided at the fluid outlet hole of the balloon.

4. A medical guiding microtube according to claim 2, wherein a pipe comprising non-X ray transmission material connects the balloon with the tube.

* * * * *